(12) United States Patent
Kumar et al.

(10) Patent No.: US 10,479,741 B2
(45) Date of Patent: Nov. 19, 2019

(54) PROCESSES AND APPARATUS FOR ISOMERIZING HYDROCARBONS

(71) Applicant: UOP LLC, Des Plaines, IL (US)

(72) Inventors: Manoj Kumar, Gurugram (IN); David J. Shecterle, Arlington Heights, IL (US); Rohit Sachan, Haryana (IN); Shone Abraham, Delhi (IN); Rajaraman Panchapakesan, Haryana (IN); Kiran Ladkat, Haryana (IN); Pankaj Kumar Singh, Delhi (IN); Mohamed S. M. Shakur, Hoffman Estates, IL (US); Emily A. Harrell, Whitsett, NC (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/813,057

(22) Filed: Nov. 14, 2017

(65) Prior Publication Data

US 2019/0144360 A1      May 16, 2019

(51) Int. Cl.
*C07C 5/27*      (2006.01)
*C07C 5/22*      (2006.01)
(Continued)

(52) U.S. Cl.
CPC .......... *C07C 5/277* (2013.01); *B01D 53/1456* (2013.01); *C07C 5/2702* (2013.01); *C07C 7/11* (2013.01)

(58) Field of Classification Search
CPC .................................................. B01D 53/1456
(Continued)

(56) References Cited

U.S. PATENT DOCUMENTS 2,414,371 A * 1/1947 Fragen .................. C07C 5/2253
                                                                196/132
2,433,482 A * 12/1947 Roberts ................. C07C 5/2721
                                                                585/738
(Continued)

FOREIGN PATENT DOCUMENTS

GB           610009 A         10/1948

OTHER PUBLICATIONS

International Search Report from corresponding PCT application No. PCT/US2018/060687, dated Feb. 28, 2019.
(Continued)

*Primary Examiner* — Youngsul Jeong

(57) ABSTRACT

Processes and apparatus for isomerizing hydrocarbons are provided. The process comprises isomerizing at least a portion of the hydrocarbon feed stream comprising at least one of $C_4$ to $C_7$ hydrocarbons in the presence of an isomerization catalyst and hydrogen under isomerization conditions to produce a isomerized stream. The isomerized stream is stabilized in a stabilizer to provide a stabilizer off-gas stream comprising chlorides and a liquid isomerate stream. At least a portion of the stabilizer off-gas stream is contacted with an exchange stream to provide an absorber overhead stream and absorber bottoms stream comprising chlorides. The absorber bottoms stream is passed to the isomerization reactor. The liquid isomerate stream is passed to a deisohexanizer column to provide an isomerate product and deisohexanizer side stream.

20 Claims, 2 Drawing Sheets

(51) Int. Cl.
  *B01D 53/14* (2006.01)
  *B01D 53/00* (2006.01)
  *C07C 7/11* (2006.01)

(58) Field of Classification Search
  USPC .................. 585/253, 477, 671, 734, 738
  See application file for complete search history.

(56) References Cited

U.S. PATENT DOCUMENTS

| | | |
|---|---|---|
| 2,454,149 A | 11/1948 | Franklin et al. |
| 2,786,086 A | 3/1957 | Morris |
| 2,946,736 A * | 7/1960 | Muffat .................. C10G 59/02 |
| | | 208/57 |
| 3,156,738 A | 11/1964 | Reveal et al. |
| 3,227,776 A | 1/1966 | Ross |
| 3,271,467 A | 9/1966 | Nakayama |
| 3,441,498 A * | 4/1969 | Jubin .................. B01J 8/22 |
| | | 208/143 |
| 4,275,257 A | 6/1981 | Hutson |
| 4,374,654 A * | 2/1983 | McCoy .................. B01D 53/04 |
| | | 423/230 |
| 4,432,862 A | 2/1984 | Swart et al. |
| 8,841,499 B2 * | 9/2014 | Kumar .................. C07C 5/277 |
| | | 585/302 |
| 2013/0096356 A1 * | 4/2013 | Bharuka .................. C07C 9/14 |
| | | 585/317 |
| 2013/0225886 A1 * | 8/2013 | Gajda .................. C10G 59/06 |
| | | 585/302 |
| 2016/0101795 A1 | 4/2016 | Pigourier et al. |

OTHER PUBLICATIONS

Written Opinion from corresponding PCT application No. PCT/US2018/060687, dated Feb. 7, 2019.

* cited by examiner

PROCESSES AND APPARATUS FOR ISOMERIZING HYDROCARBONS

FIELD

The subject matter of the present disclosure generally relates to processes and apparatus for isomerizing hydrocarbons and more particularly relates to minimizing chloride and caustic consumption in a process and apparatus for isomerizing hydrocarbons.

BACKGROUND

Isomerization catalyst requires a continuous injection of chlorides to maintain the acid sites activity at a rate of 150 wppm of combined feed to isomerization reactors such as in UOP PENEX™ processes. The chlorides injected to the isomerization reactors result in the presence of hydrogen chloride and/or other chlorinated compounds in the gaseous and liquid effluents obtained from the isomerization unit, which inevitably leads to corrosion of the facilities, formation of deposits or salts based on chlorine, or accelerated contamination of catalysts which might be located downstream of the isomerization unit. Thus, it is important to eliminate all traces of hydrogen chloride or other chlorinated compounds from these effluents.

Typically, such chlorides are scrubbed with a caustic solution in a net gas scrubber (NGS) before sending off gases to a fuel gas header or alternate destinations. This requires large amounts of caustic consumption on a continuous basis and refiners want to reduce the treatment cost of spent caustic. Caustic handling and treatment is an environmental concern and is cost intensive.

Therefore, there is a need for improved processes and apparatus for efficiently handling the chlorine injected into the isomerization process and reducing net chloride consumption. Further, it is desirable to reduce caustic consumption in the overall process, thereby decreasing associated costs. Other desirable features and characteristics of the present subject matter will become apparent from the subsequent detailed description of the subject matter and the appended claims, taken in conjunction with the accompanying drawings and this background of the subject matter.

SUMMARY

Various embodiments contemplated herein relate to processes and apparatuses for isomerizing hydrocarbons. The exemplary embodiments taught herein minimize chloride and caustic consumption in processes and apparatus for isomerizing hydrocarbons.

In accordance with an exemplary embodiment, a process is provided for isomerizing a hydrocarbon feed stream comprising at least one of $C_4$ to $C_7$ hydrocarbons. The process comprises isomerizing a first portion of the hydrocarbon feed stream in the presence of an isomerization catalyst and hydrogen in an isomerization reactor under isomerization conditions to produce an isomerized stream. The isomerized stream is stabilized in a stabilizer unit to provide a stabilizer off-gas stream comprising chlorides and a liquid isomerate stream. A second portion of the hydrocarbon feed stream is cooled to a temperature of about $-40°$ F. to about $20°$ F. to provide a chilled hydrocarbon feed. A first portion of the stabilizer off-gas stream is contacted with the chilled hydrocarbon feed in an absorber column to provide an absorber overhead stream and an absorber bottoms stream comprising chlorides. Subsequently, the absorber bottoms stream is passed to the isomerization reactor.

In accordance with another exemplary embodiment, a process is provided for isomerizing a hydrocarbon feed stream comprising at least one of $C_4$ to $C_7$ hydrocarbons. The process comprises isomerizing at least a portion of the hydrocarbon feed stream in the presence of an isomerization catalyst and hydrogen in an isomerization reactor under isomerization conditions to produce an isomerized stream. The isomerized stream is stabilized in a stabilizer unit to provide a stabilizer off-gas stream comprising chlorides and a liquid isomerate stream. The liquid isomerate stream is passed to a deisohexanizer column to provide an isomerate product and a deisohexanizer side stream. A portion of the stabilizer off-gas stream is contacted with a portion of the deisohexanizer side draw stream in an absorber column to provide an absorber overhead stream and an absorber bottoms stream comprising chlorides. Subsequently, the absorber bottoms stream is passed to the isomerization reactor.

The disclosed subject matter allows recovering the chlorides from stabilizer vapors and recycling it back to the isomerization reactor section to minimize the net chloride consumption and therefore minimize the caustic consumption.

These and other features, aspects, and advantages of the present disclosure will become better understood upon consideration of the following detailed description, drawings and appended claims.

BRIEF DESCRIPTION OF THE DRAWINGS

The various embodiments will hereinafter be described in conjunction with the following drawing figures, wherein like numerals denote like elements, and wherein.

Figure 1:
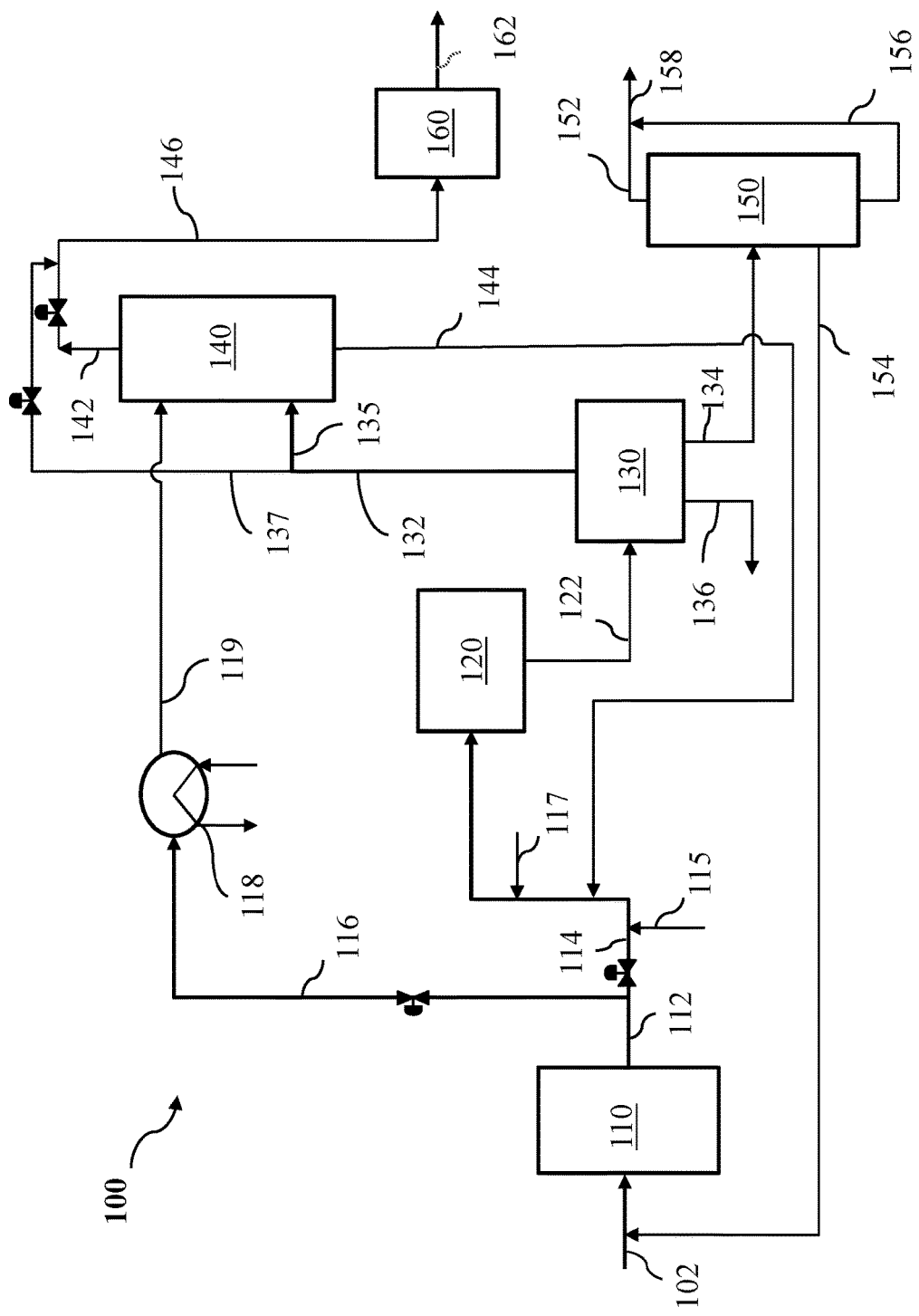
FIG. 1 is a schematic diagram of a process and an apparatus for isomerizing hydrocarbons in accordance with an exemplary embodiment.

Skilled artisans will appreciate that elements in the FIGURES are illustrated for simplicity and clarity and have not necessarily been drawn to scale. For example, the dimensions of some of the elements in the FIGURES may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

The following detailed description is merely exemplary in nature and is not intended to limit the various embodiments or the application and uses thereof. Furthermore, there is no intention to be bound by any theory presented in the preceding background or the following Processes and apparatus for isomerizing hydrocarbons are provided herein. The process comprises isomerizing at least a portion of a hydrocarbon feed stream comprising at least one of $C_4$ to $C_7$ hydrocarbons in the presence of an isomerization catalyst and hydrogen under isomerization conditions to produce an isomerized stream. The isomerized stream is stabilized in a stabilizer to provide a stabilizer off-gas stream comprising chlorides and a liquid isomerate stream. At least a portion of the stabilizer off-gas stream is contacted with an exchange stream to provide an absorber overhead stream and absorber bottoms stream comprising chlorides. The absorber bottoms stream is passed to the isomerization reactor. The liquid isomerate stream is passed to a deisohexanizer column to provide an isomerate product and deisohexanizer side stream. The exchange stream may be a portion of the hydrocarbon feed-stream to the isomerization reactor or a side draw from the deisohexanizer column located downstream of the isomerization reactor.

As depicted, process flow lines in the FIGURES can be referred to, interchangeably, as, e.g., lines, pipes, branches, distributors, streams, effluents, feeds, products, portions, catalysts, withdrawals, recycles, suctions, discharges, and caustics.

As used herein, the term "unit" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "vapor" can mean a gas or a dispersion that may include or consist of one or more hydrocarbons.

As used herein, the term "stream" can include various hydrocarbon molecules and other substances. Moreover, the term "stream comprising Cx hydrocarbons" can include a stream comprising hydrocarbon with "x" number of carbon atoms, suitably a stream with a majority of hydrocarbons with "x" number of carbon atoms and preferably a stream with at least 75 wt % hydrocarbon molecules, respectively, with "x" number of carbon atoms. Moreover, the term "stream comprising Cx+ hydrocarbons" can include a stream comprising a majority of hydrocarbon molecules, with more than or equal to "x" carbon atoms and suitably less than 10 wt % and preferably less than 1 wt % hydrocarbon molecules, with x−1 carbon atoms. Lastly, the term "Cx− stream" can include a stream comprising a majority of hydrocarbon molecules with less than or equal to "x" carbon atoms and suitably less than 10 wt % and preferably less than 1 wt % hydrocarbon molecules, with x+1 carbon atoms.

As used herein, the term "overhead stream" can mean a stream withdrawn at or near a top of a vessel, such as a column.

The term "column" means a distillation column or columns for separating one or more components of different volatilities. Unless otherwise indicated, each column includes a condenser on an overhead of the column to condense the overhead vapor and reflux a portion of an overhead stream back to the top of the column. Also included is a reboiler at a bottom of the column to vaporize and send a portion of a bottom stream back to the bottom of the column to supply fractionation energy. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

As used herein, the term "bottoms stream" can mean a stream withdrawn at or near a bottom of a vessel, such as a column.

As used herein, the term "substantially" can mean an amount of generally at least about 90%, preferably about 95%, and optimally about 99%, by mole, of a compound or class of compounds in a stream.

An exemplary embodiment of the process and apparatus for isomerizing hydrocarbons is addressed with reference to a process and apparatus 100 according to an embodiment as shown in FIG. 1. The process and apparatus 100 includes a drier 110, an isomerization reactor 120, a stabilizer unit 130, an absorber column 140, a deisohexanizer column 150 and a scrubber 160.

In accordance with an exemplary embodiment as shown in FIG. 1, a hydrocarbon feed stream in line 102 may be passed to the drier 110. Drying is generally carried out by adsorption over a molecular sieve. A deisohexanizer side draw stream in line 154 may also be mixed to the hydrocarbon feed stream prior to being passed to the drier 110. The hydrocarbon feed stream may be a feed comprising at least one of $C_4$-$C_7$ hydrocarbons. In one embodiment, the hydrocarbon feed stream may include predominantly $C_5$ and $C_6$ hydrocarbons. In another embodiment, the hydrocarbon feed stream may include predominantly $C_4$ hydrocarbons. In yet another embodiment, the hydrocarbon feed stream may include predominantly $C_7$ hydrocarbons. In still another embodiment, the hydrocarbon feed stream may comprise $C_5$, $C_6$ and $C_7$ hydrocarbons. For the purposes of discussion of the instant embodiment, the hydrocarbon feed stream may include predominantly $C_5$ and $C_6$ hydrocarbons.

A dry hydrocarbon feed stream is obtained in line 112 which is subsequently processed. As shown in the FIG. 1, the dry hydrocarbon feed stream is split into a first portion of hydrocarbon feed stream in line 114 and a second portion of hydrocarbon feed stream in line 116. One or more valves may be placed on the first hydrocarbon line 114 and the second hydrocarbon line 116 to control the percentage split of the hydrocarbon feed stream. The second portion of the hydrocarbon feed stream is about 20 to about 40 wt %, or about 20 to about 35 wt %, or about 25 to about 35 wt % of the hydrocarbon feed stream. The first portion of the hydrocarbon feed stream in line 114 may be isomerized in the isomerization reactor 120 in the presence of an isomerization catalyst and hydrogen under isomerization conditions. As shown, a make-up hydrogen gas in line 115 and a chloride compound such as hydrogen chloride in line 117 may be introduced to the first portion in line 114 before being passed to the isomerization reactor 120. Further, an absorber bottoms stream in line 144 may be injected to the first portion in line 114 before being passed to the isomerization reactor 120.

An isomerized stream in line 122 is withdrawn from the isomerization reactor 120 which may be passed to the stabilizer unit 130. Separation is carried out in the stabilizer unit to provide a stabilizer off-gas stream in line 132 comprising chlorides and a liquid isomerate stream in line 134. Further, an intermediate stream comprising $C_3$ and $C_4$ hydrocarbons (LPG) may be withdrawn in line 136 in order to reduce build-up of LPG in the system. Although not shown, the stabilizer unit 130 may include a chiller on stabilizer receiver off-gas and an LPG stripper with a shared overhead system with the stabilizer unit 130 to provide the intermediate stream comprising $C_3$ and $C_4$ hydrocarbons in line 136.

Referring back to the second portion of the hydrocarbon feed stream in line 116, the second portion in line 116 may be passed through the chiller 118 to provide a chilled hydrocarbon feed stream in line 119. The second portion in line 116 may be cooled to a temperature of about −40° F. to about 20° F., or about −40° F. to about −0° F., or about −10° F. to about 10° F. to provide the chilled hydrocarbon feed stream.

At least a portion of the stabilizer off-gas stream is contacted with the chilled hydrocarbon feed stream in the absorber column 140 to provide an absorber overhead stream in line 142 and an absorber bottoms stream in line 144 comprising chlorides. The remaining portion of the stabilizer off-gas may bypass the absorber column 140 and may be passed to the scrubber 160. As shown in FIG. 1, a first portion of the stabilizer off-gas stream in line 135 may be passed to the absorber column 140 and a second portion of the stabilizer off-gas stream in line 137 may bypass the absorber column 140. The second portion of the stabilizer off-gas stream may be about 10 to about 40%, or about 10 to about 15%, of the stabilizer off-gas stream. One or more valves may be placed on the second portion of the stabilizer off-gas in line 137 to control the portion of the stabilizer off-gas bypassing the absorber column 140. In one example, at least a portion of the second portion of the stabilizer off-gas may be recycled (not shown) to the isomerization reactor 120. In an aspect, the at least a portion of the second portion of the stabilizer off-gas may be recycled to the isomerization reactor 120 by passing through an eductor (not shown) upstream of the isomerization reactor. The at least a portion of the second portion of the stabilizer off-gas being recycled is about 50 to about 80 wt % of the second portion of the stabilizer off-gas stream. In an embodiment, the absorber overhead stream in line 142 may be passed through an additional chiller (not shown) on an overhead of the absorber column 142. Applicants have found that the absorber overhead stream comprises small amount of $C_{5+}$ hydrocarbons. The additional chiller condenses the $C_{5+}$ hydrocarbons present in the absorber overhead stream to provide a condensed stream which may be subsequently passed back to absorber column with a net portion of the absorbed overhead stream, substantially free of $C_{5+}$ hydrocarbons, being passed to the scrubber 160. Accordingly, the presence of an additional chiller on the absorber overhead prevents loss of $C_{5+}$ hydrocarbons.

Referring back to the absorber column 140, the first portion of the stabilizer off-gas stream in line 135 and the chilled hydrocarbon feed stream in line 119 may be introduced at separate locations in the absorber column 140 as shown in FIG. 1. The contacting in the absorber column 140 may take place at an operating pressure of about 160-300 psig, or from about 180-220 psig. The chilled hydrocarbon feed stream absorbs the chloride compounds from the first portion of the stabilizer off-gas stream and provides the absorber bottoms stream in line 144 including the chloride compounds. The absorber bottoms stream in line 144 may be passed to the isomerization reactor 120. In an embodiment, the absorber bottoms stream may be heated via heat exchange with the deisohexanizer side draw stream in line 154 before being passed to the isomerization reactor 120. As shown in the FIG. 1, the absorber bottoms stream may be mixed with the first portion of the hydrocarbon stream in line 114 and passed to the isomerization reactor 120.

The absorber overhead stream in line 142 may be passed to the scrubber 160. As shown in FIG. 1, the second portion of the stabilizer off-gas in line 137 bypassing the absorber column 140 may also be introduced to the absorber overhead stream or net portion of the absorber overhead stream to provide a combined stream in line 146. In one example, at least a portion of the combined stream in line 146 may be recycled (not shown) to the isomerization reactor 120. In an aspect, the portion of the combined stream may be recycled to the isomerization reactor by passing through an eductor upstream of the isomerization reactor. The portion of the combined stream being recycled is about 50 to about 80 wt % of the combined stream. In one embodiment, the absorber overhead stream or the net portion of the absorber overhead stream and the second portion of the stabilizer off-gas stream may be introduced separately to the scrubber 160. The incoming feed streams to the scrubber 160 are treated with a caustic stream (not shown) to remove any chloride compounds and provide a chloride free off-gas in line 162.

Referring back to stabilizer unit 130, the liquid isomerate line in 134 may be passed to the deisohexanizer column 150 for separation. The deisohexanizer side draw stream in line 154 comprising linear hexane, cyclic hydrocarbons, and monomethyl-branched pentane is withdrawn from the deisohexanizer column 150 and recycled to combine with the hydrocarbon feed stream in line 102. The pentanes, dimethyl-butanes, and some monomethyl alkanes removed in deisohexanizer overhead stream in line 152 are combined with the $C_6$ naphthenes and $C_{7+}$ in deisohexanizer bottoms stream in line 156 to form the isomerate product stream in line 158.

Further, in accordance with an exemplary embodiment, applicants have found that the combined stream including the absorber overhead stream or the net portion of the absorber overhead stream and the second portion of the stabilizer off-gas stream bypassing the absorber column may be directly passed to spent catalyst in a catalytic reforming unit (not shown). In such an embodiment, the scrubber 160 may not be required.

Figure 2:
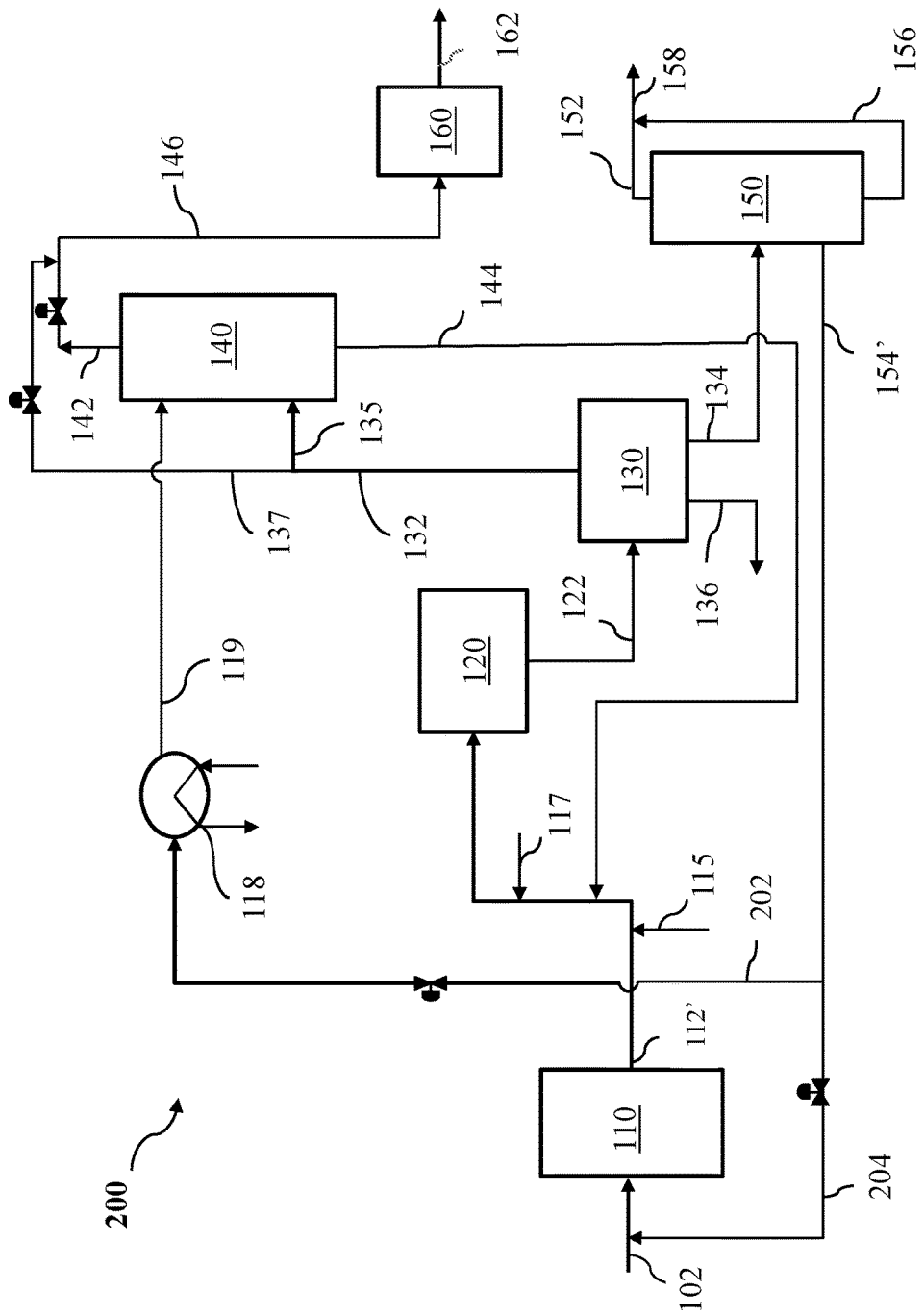
FIG. 2 is a schematic diagram of a process and an apparatus for isomerizing hydrocarbons in accordance with an exemplary embodiment.

Turning now to FIG. 2, another exemplary embodiment of the process and apparatus for isomerizing hydrocarbons is addressed with reference to a process and apparatus 200. Many of the elements in the FIG. 2 have the same configuration as in FIG. 1 and bear the same respective reference number and have similar operating conditions. Elements in FIG. 2 that correspond to elements in FIG. 1 but have a different configuration bear the same reference numeral as in FIG. 1 but are marked with a prime symbol ('). The apparatus and process in FIG. 2 are the same as in FIG. 1 with the exception of the noted following differences. In accordance with the exemplary embodiment as shown in the FIG. 2, the hydrocarbon feed stream in line 112' may be passed to the isomerization reactor 120 to isomerize the hydrocarbon feed stream in the presence of an isomerization catalyst and hydrogen under isomerization conditions to produce the isomerized stream in line 122 which is processed further as described in FIG. 1.

In the instant embodiment, the first portion of the stabilizer off-gas stream is contacted with a portion of the deisohexanizer side draw stream in the absorber column 140. As shown in FIG. 2, a deisohexanizer side stream in line 154' may be split into a first portion of deisohexanizer side draw stream in line 202 and a second portion of deisohexanizer side draw stream in line 204. One or more valves may be placed on the first deisohexanizer side draw line 202 and the second deisohexanizer side draw line 204 to control the percentage split of the deisohexanizer side draw stream. The second portion of the deisohexanizer side draw stream is about 40 to about 80 wt %, or about 50 to about 70 wt % of the deisohexanizer side draw stream. The first portion of the deisohexanizer side draw stream in line 202 may be passed through the chiller 118 to provide the chilled hydrocarbon stream line 119. As shown in FIG. 2, the first portion of the stabilizer off-gas stream in line 135 is contacted with the chilled hydrocarbon stream in line 119 to provide the absorber overhead stream in line 142 and absorber bottoms stream comprising chlorides in line 144 which are process further as described in FIG. 1. The second portion of deisohexanizer side draw stream in line 204 may be introduced to hydrocarbon feed stream in line 102 and passed to the drier 110 to provide the hydrocarbon feed stream in line 112'. Rest of the process is similar to as described in FIG. 1.

It has been found that the overall chloride injection rate i.e. amount of chloride compounds required and caustic consumption with proposed flow scheme as disclosed in the present disclosure can be reduced to approximately 15% as compared to conventional schemes. Further, the proposed flow scheme results in higher LPG production due to recovery of $C_3$ & $C_4$s from off gases in addition to HCl in the absorber column.

Applicants have found that the percentage recovery of hydrogen chloride from stabilizer off-gas, across the absorber column, varies with the variation in the amount of the second portion of the hydrocarbon feed stream being passed to the absorber column i.e. the liquid flow to the absorber column, for various chiller temperatures. Applicants have found that the optimum amount of the second portion of the hydrocarbon feed being bypassed around the isomerization reactor is about 20 wt % to about 35 wt %, with any further increase resulting in diminishing returns as the increase in hydrogen chloride recovery is very small. For example, Table 1 shows that optimum hydrogen chloride recovery occurs when the second portion of the hydrocarbon feed stream is about 20 wt % to about 25 wt % of the hydrocarbon feed stream at a chiller temperature of about 0° F. Below 20 wt %, the recovery is much less. Above 25 wt %, the recovery reaches near maximum and any further feed split, results in diminishing returns. At a chiller outlet temperature of about 40° F., optimum recovery of hydrogen chloride occurs when the second portion of the hydrocarbon feed stream being bypassed around the isomerization reactor is from about 20 wt % to about 35 wt % of the hydrocarbon feed stream as shown in Table 2.

TABLE 1

| Liquid flow to Absorber column (% of combined feed) | Absorber Operating Conditions | | | % HCL |
|---|---|---|---|---|
| | Chiller Outlet Temp, ° F. | Press, psig | Stages | Recovery Across Absorber column |
| 10% | 0 | 200 | 10 | 38.82% |
| 15% | 0 | 200 | 10 | 51.49% |
| 20% | 0 | 200 | 10 | 96.00% |
| 25% | 0 | 200 | 10 | 99.63% |
| 30% | 0 | 200 | 10 | 99.93% |
| 35% | 0 | 200 | 10 | 99.98% |
| 40% | 0 | 200 | 10 | 99.99% |
| 45% | 0 | 200 | 10 | 100.00% |

TABLE 2

| Liquid flow to Absorber column (% of combined feed) | Absorber Operating Conditions | | | % HCl |
|---|---|---|---|---|
| | Chiller Outlet Temp, ° F. | Press, psig | Stages | Recovery Across Absorber column |
| 10% | 40 | 200 | 10 | 34.40% |
| 15% | 40 | 200 | 10 | 43.80% |
| 20% | 40 | 200 | 10 | 55.70% |
| 25% | 40 | 200 | 10 | 89.10% |
| 30% | 40 | 200 | 10 | 97.30% |
| 35% | 40 | 200 | 10 | 99.20% |
| 40% | 40 | 200 | 10 | 99.70% |
| 45% | 40 | 200 | 10 | 99.94% |

Further, Table 3 illustrates the change in percentage recovery of HCl across the absorber column with variation in chiller outlet temperature. As shown in Table 3, applicants have found that hydrogen chloride recovery shows a significant decrease and goes below 96 wt % when the chiller temperature goes about 20° F. Accordingly, applicants have found out that the optimum chiller temperature should be in the range of −40° F. to about 20° F. to get the desired HCl recovery

TABLE 3

| Liquid flow to Absorber column (% of combined feed) | Absorber Operating Conditions | | | % HCl |
|---|---|---|---|---|
| | Chiller Outlet Temp, ° F. | Press, psig | Stages | Recovery Across Absorber column |
| 25% | −40 | 200 | 10 | 99.99% |
| 25% | −30 | 200 | 10 | 99.95% |
| 25% | −20 | 200 | 10 | 99.90% |
| 25% | −10 | 200 | 10 | 99.80% |
| 25% | 0 | 200 | 10 | 99.60% |
| 25% | 10 | 200 | 10 | 99.10% |
| 25% | 20 | 200 | 10 | 97.93% |
| 25% | 30 | 200 | 10 | 95.55% |
| 25% | 40 | 200 | 10 | 91.05% |
| 25% | 60 | 200 | 10 | 71.24% |
| 25% | 80 | 200 | 10 | 51.75% |
| 25% | 100 | 200 | 10 | 48.89% |

Further, the process as disclosed in the present disclosure as illustrated in FIG. 1 and FIG. 2, results in savings 10.4 MMUSD per year as compared to conventional schemes with no absorber and savings of 1.1 MMUSD as compared to scheme having an absorber without chillers.

Also, applicants have established the use of the eductor as disclosed in the present disclosure to partially recycle the off gas coming from the absorber column overhead stream or the combined stream to the isomerization reactor. In current practice, this recycle is being achieved by a compressor. The use of eductor helps to achieve this recycle without using any moving part and hence providing additional savings in CAPEX.

SPECIFIC EMBODIMENTS

While the following is described in conjunction with specific embodiments, it will be understood that this description is intended to illustrate and not limit the scope of the preceding description and the appended claims.

A first embodiment of the invention is a process for isomerizing a hydrocarbon feed stream comprising at least one of $C_4$ to $C_7$ hydrocarbons, wherein the process comprises isomerizing a first portion of the hydrocarbon feed stream in the presence of an isomerization catalyst and hydrogen in an isomerization reactor under isomerization conditions to produce an isomerized stream; stabilizing the isomerized stream in a stabilizer unit to provide a stabilizer off-gas stream comprising chlorides and a liquid isomerate stream; cooling a second portion of the hydrocarbon feed stream to a temperature of about −40° F. to about 20° F. to provide a chilled hydrocarbon feed stream; contacting a first portion of the stabilizer off-gas stream with the chilled hydrocarbon feed stream in an absorber column to provide an absorber overhead stream and absorber bottoms stream comprising chlorides; and passing the absorber bottoms stream to the isomerization reactor. An embodiment of the invention is one, any or all of prior embodiments in this paragraph up through the first embodiment in this paragraph, wherein the second portion of the hydrocarbon feed stream is cooled to a temperature of about −10° F. to about 10° F to provide the chilled hydrocarbon feed stream. An embodiment of the invention is one, any or all of prior embodiments in this paragraph up through the first embodiment in this paragraph, wherein the second portion of the hydrocarbon feed stream is about 20 to about 35 wt % of the hydrocarbon feed stream. An embodiment of the invention is one, any or all of prior embodiments in this paragraph up through the first embodiment in this paragraph further comprising bypassing a second portion of the stabilizer off-gas stream around the absorber. An embodiment of the invention is one, any or all of prior embodiments in this paragraph up through the first embodiment in this paragraph, wherein the second portion of the stabilizer off-gas stream comprises about 10 to about 40% of the stabilizer off-gas stream. An embodiment of the invention is one, any or all of prior embodiments in this paragraph up through the first embodiment in this paragraph further comprising passing the absorber overhead stream to an additional chiller to provide a condensed stream being passed back to the absorber column and a net portion of the absorber overhead stream being passed to a scrubber. An embodiment of the invention is one, any or all of prior embodiments in this paragraph up through the first embodiment in this paragraph, wherein the contacting takes place in the absorber column at an operating pressure of about 160-300 psig. An embodiment of the invention is one, any or all of prior embodiments in this paragraph up through the first embodiment in this paragraph further comprising splitting the hydrocarbon feed stream to provide the first portion of the hydrocarbon feed stream and the second portion of the hydrocarbon feed stream. An embodiment of the invention is one, any or all of prior embodiments in this paragraph up through the first embodiment in this paragraph, wherein the absorber bottoms stream is passed downstream of the splitting of the hydrocarbon feed stream. An embodiment of the invention is one, any or all of prior embodiments in this paragraph up through the first embodiment in this paragraph further comprising recycling at least one of a portion of the absorber overhead stream and a portion of the second portion of the stabilizer off-gas stream to the isomerization reactor by passing through an eductor upstream of the isomerization reactor. An embodiment of the invention is one, any or all of prior embodiments in this paragraph up through the first embodiment in this paragraph further comprising passing at least a portion of the absorber overhead stream and the second portion of the stabilizer off-gas stream to spent catalyst in a catalytic reforming unit.

A second embodiment of the invention is a process for isomerizing a hydrocarbon feed stream comprising at least one of $C_4$ to $C_7$ hydrocarbons, wherein the process comprises isomerizing at least a portion of the hydrocarbon feed stream in the presence of an isomerization catalyst and hydrogen in an isomerization reactor under isomerization conditions to produce an isomerized stream; stabilizing the isomerized stream in a stabilizer unit to provide a stabilizer off-gas stream comprising chlorides and a liquid isomerate stream; passing the liquid isomerate stream to a deisohexanizer column to provide an isomerate product and a deisohexanizer side stream; contacting a first portion of the stabilizer off-gas stream with a first portion of the deisohexanizer side draw stream in an absorber column to provide an absorber overhead stream and absorber bottoms stream comprising chlorides; and passing the absorber bottoms stream to the isomerization reactor. An embodiment of the invention is one, any or all of prior embodiments in this paragraph up through the second embodiment in this paragraph further comprising cooling the first portion of the deisohexanizer side draw stream to a temperature of about −40° F. to about 20° F. before being passed to absorber column for the contacting step. An embodiment of the invention is one, any or all of prior embodiments in this paragraph up through the second embodiment in this paragraph further comprising passing a second portion of the deisohexanizer side draw stream to the isomerization reactor. An embodiment of the invention is one, any or all of prior embodiments in this paragraph up through the second embodiment in this paragraph further comprising bypassing a second portion of the stabilizer off-gas stream around the absorber column. An embodiment of the invention is one, any or all of prior embodiments in this paragraph up through the second embodiment in this paragraph, wherein the second portion of the stabilizer off-gas stream comprises about 10 to about 40% of the stabilizer off-gas stream. An embodiment of the invention is one, any or all of prior embodiments in this paragraph up through the second embodiment in this paragraph further comprising passing the absorber overhead stream to an additional chiller to provide a condensed stream being passed back to the absorber column and a net portion of the absorber overhead stream being passed to a scrubber. An embodiment of the invention is one, any or all of prior embodiments in this paragraph up through the second embodiment in this paragraph further comprising recycling at least one of a portion of the absorber overhead stream and a portion of the second portion of the stabilizer off-gas stream to the isomerization reactor by passing through an eductor upstream of the isomerization reactor. An embodiment of the invention is one, any or all of prior embodiments in this paragraph up through the second embodiment in this paragraph further comprising passing at least a portion of the absorber overhead stream and the second portion of the stabilizer off-gas stream to spent catalyst in a catalytic reforming unit. An embodiment of the invention is one, any or all of prior embodiments in this paragraph up through the second embodiment in this paragraph, wherein the contacting takes place in the absorber column at an operating pressure of about 160 psig to about 300 psig.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Fahrenheit and, all parts and percentages are by weight, unless otherwise indicated.

The invention claimed is:

1. A process for isomerizing a hydrocarbon feed stream comprising at least one of $C_4$ to $C_7$ hydrocarbons, wherein the process comprises:
    isomerizing a first portion of the hydrocarbon feed stream in the presence of an isomerization catalyst and hydrogen in an isomerization reactor under isomerization conditions to produce an isomerized stream;
    stabilizing the isomerized stream in a stabilizer unit to provide a stabilizer off-gas stream comprising chlorides and a liquid isomerate stream;
    cooling a second portion of the hydrocarbon feed stream to a temperature of about −40° F. to about 20° F. to provide a chilled hydrocarbon feed stream;
    contacting a first portion of the stabilizer off-gas stream with the chilled hydrocarbon feed stream in an absorber column to provide an absorber overhead stream and an absorber bottoms stream comprising chlorides; and
    passing the absorber bottoms stream to the isomerization reactor.

2. The process of claim 1, wherein the second portion of the hydrocarbon feed stream is cooled to a temperature of about −10° F. to about 10° F. to provide the chilled hydrocarbon feed stream.

3. The process of claim 1, wherein the second portion of the hydrocarbon feed stream is about 20 to about 35 wt % of the hydrocarbon feed stream.

4. The process of claim 1 wherein a second portion of the stabilizer off-gas stream bypasses the absorber column.

5. The process of claim 4, wherein the second portion of the stabilizer off-gas stream comprises about 10 to about 40% of the stabilizer off-gas stream.

6. The process of claim 1 further comprising passing the absorber overhead stream to an additional chiller to provide a condensed stream which is passed back to the absorber column and a net portion of the absorber overhead stream being passed to a scrubber.

7. The process of claim 1, wherein the contacting takes place in the absorber column at an operating pressure of about 1103 to 2068 kPa (160 to 300 psig).

8. The process of claim 1 further comprising splitting the hydrocarbon feed stream to provide the first portion of the hydrocarbon feed stream and the second portion of the hydrocarbon feed stream.

9. The process of claim 8, wherein the absorber bottoms stream is passed downstream of the splitting of the hydrocarbon feed stream.

10. The process of claim 1 further comprising recycling at least one of a portion of the absorber overhead stream and a portion of a second portion of the stabilizer off-gas stream to the isomerization reactor by passing through an eductor upstream of the isomerization reactor.

11. The process of claim 1 further comprising passing at least a portion of the absorber overhead stream and a second portion of the stabilizer off-gas stream to a spent catalyst in a catalytic reforming unit.

12. A process for isomerizing a hydrocarbon feed stream comprising at least one of $C_4$ to $C_7$ hydrocarbons, wherein the process comprises:
    isomerizing at least a portion of the hydrocarbon feed stream in the presence of an isomerization catalyst and hydrogen in an isomerization reactor under isomerization conditions to produce an isomerized stream;
    stabilizing the isomerized stream in a stabilizer unit to provide a stabilizer off-gas stream comprising chlorides and a liquid isomerate stream;
    passing the liquid isomerate stream to a deisohexanizer column to provide an isomerate product and a deisohexanizer side draw stream;
    contacting a first portion of the stabilizer off-gas stream with a first portion of the deisohexanizer side draw stream in an absorber column to provide an absorber overhead stream and an absorber bottoms stream comprising chlorides;
    cooling the first portion of the deisohexanizer side draw stream to a temperature of about −40° C. to about −7° C. (−40° F. to about 20° F.) before passing the first portion of the deisohexanizer side draw stream to the absorber column for the contacting step; and
    passing the absorber bottoms stream to the isomerization reactor.

13. The process of claim 12 further comprising passing a second portion of the deisohexanizer side draw stream to the isomerization reactor.

14. The process of claim 12 wherein a second portion of the stabilizer off-gas stream bypasses the absorber column.

15. The process of claim 14, wherein the second portion of the stabilizer off-gas stream comprises about 10 to about 40% of the stabilizer off-gas stream.

16. The process of claim 12 further comprising passing the absorber overhead stream to an additional chiller to provide a condensed stream and passing the condensed stream back to the absorber column and a net portion of the absorber overhead stream being passed to a scrubber.

17. The process of claim 12 further comprising recycling at least one of a portion of the absorber overhead stream and a portion of a second portion of the stabilizer off-gas stream to the isomerization reactor by passing through an eductor upstream of the isomerization reactor.

18. The process of claim 12 further comprising passing at least a portion of the absorber overhead stream and a second portion of the stabilizer off-gas stream to a spent catalyst in a catalytic reforming unit.

19. The process of claim 12, wherein the contacting takes place in the absorber column at an operating pressure of about 1103 kPa (about 160 psig) to about 2068 kPa (about 300 psig).

20. A process for isomerizing a hydrocarbon feed stream comprising at least one of $C_4$ to $C_7$ hydrocarbons, wherein the process comprises:
    isomerizing at least a portion of the hydrocarbon feed stream in the presence of an isomerization catalyst and hydrogen in an isomerization reactor under isomerization conditions to produce an isomerized stream;
    stabilizing the isomerized stream in a stabilizer unit to provide a stabilizer off-gas stream comprising chlorides and a liquid isomerate stream,
    passing the liquid isomerate stream to a deisohexanizer column to provide an isomerate product and a deisohexanizer side draw stream;
    contacting a first portion of the stabilizer off-gas stream with a first portion of the deisohexanizer side draw stream in an absorber column to provide an absorber overhead stream and an absorber bottoms stream comprising chlorides;
    passing the absorber overhead stream to an additional chiller to provide a condensed stream which is passed back to the absorber column and a net portion of the absorber overhead stream which is passed to a scrubber; and
    passing the absorber bottoms stream to the isomerization reactor.

* * * * *